United States Patent
Tsuchimoto et al.

(10) Patent No.: US 10,028,681 B2
(45) Date of Patent: Jul. 24, 2018

(54) BIOLOGICAL SENSOR

(71) Applicant: MURATA MANUFACTURING CO., LTD., Nagaokakyo-Shi, Kyoto-Fu (JP)

(72) Inventors: Hirofumi Tsuchimoto, Nagaokakyo (JP); Hiroyuki Nakaji, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 616 days.

(21) Appl. No.: 14/600,609

(22) Filed: Jan. 20, 2015

(65) Prior Publication Data

US 2015/0141840 A1 May 21, 2015

Related U.S. Application Data

(63) Continuation of application No. PCT/JP2013/065921, filed on Jun. 10, 2013.

(30) Foreign Application Priority Data

Jul. 20, 2012 (JP) ................. 2012-161296

(51) Int. Cl.
*A61B 6/00* (2006.01)
*A61B 5/1455* (2006.01)
(Continued)

(52) U.S. Cl.
CPC .......... *A61B 5/14551* (2013.01); *A61B 5/024* (2013.01); *A61B 5/02416* (2013.01); *A61B 5/7203* (2013.01)

(58) Field of Classification Search
CPC ... A61B 5/14551; A61B 5/024; A61B 5/7203; A61B 5/02416; A61B 5/0245;
(Continued)

(56) References Cited

U.S. PATENT DOCUMENTS 4,863,265 A * 9/1989 Flower ............... A61B 5/14551
356/41
5,259,381 A * 11/1993 Cheung ............... A61B 5/02427
356/41

FOREIGN PATENT DOCUMENTS

JP H02-13815 A 1/1990
JP H03-116252 A 5/1991
(Continued)

OTHER PUBLICATIONS

Written Opinion and International Search Report issued in PCT/JP2013/065921 dated Aug. 13, 2013.

*Primary Examiner* — Mallika D Fairchild
(74) *Attorney, Agent, or Firm* — Arent Fox LLP

(57) ABSTRACT

A biological sensor capable of improving the signal-to-noise ratio of a detection signal obtained by a light-receiving element and amplified by an amplifier is provided.
The biological sensor includes a driving signal generating unit that generates a pulse-form driving signal, a light-emitting element that emits light in response to the generated driving signal, a light-receiving element that outputs a detection signal based on an intensity of received light, an amplifying unit including first and second operational amplifiers that amplify the outputted detection signal, an offset signal generating unit and a voltage dividing resistor group that generate a pulse-form offset voltage for offsetting a reference potential of the first operational amplifier when amplifying the detection signal and apply the offset voltage to the first operational amplifier, and a computation unit that obtains biological information by processing the detection signal amplified by the amplifying unit.

20 Claims, 9 Drawing Sheets

(51) Int. Cl.
*A61B 5/024* (2006.01)
*A61B 5/00* (2006.01)

(58) Field of Classification Search
CPC ... A61B 5/0261; A61B 5/7264; A61B 5/0095;
A61B 5/02427; A61B 5/1455; A61B
2562/0233; A61B 2562/0238; A61N
2005/0659; A61N 2005/067; A61N
2005/0061; A61N 2005/0063; A61N
2005/0656; A61N 5/06; A61N 1/08;
A61N 1/36125; A61N 2005/0662
See application file for complete search history.

(56) References Cited

FOREIGN PATENT DOCUMENTS

| | | |
|---|---|---|
| JP | H06-063024 A | 3/1994 |
| JP | H06-154178 A | 6/1994 |
| JP | H09-24028 A | 1/1997 |
| JP | 2007-151579 A | 6/2007 |

\* cited by examiner

BIOLOGICAL SENSOR

CROSS REFERENCE TO RELATED APPLICATIONS

The present application is a continuation of PCT/JP2013/065921 filed Jun. 10, 2013, which claims priority to Japanese Patent Application No. 2012-161296, filed Jul. 20, 2012, the entire contents of each of which are incorporated herein by reference.

FIELD OF THE INVENTION

The present invention relates to biological sensors that detect biological information.

BACKGROUND OF THE INVENTION

Conventional photoelectrical sphygmographs, pulse oximeters, and the like that obtain photoelectric pulse wave signals based on changes in the intensity of light that passes through a biological body such as a finger or is reflected by the biological body by exploiting a characteristic of bloodstream hemoglobin that absorbs visible light to infrared light are known (see Patent Document 1, for example).

Here, the pulse oximeter according to Patent Document 1 includes first and second light-emitting diodes that are driven in an alternating manner by pulse signals outputted from an oscillation circuit so as to irradiate biological tissue with red light and infrared light, and a photodiode that detects a light output after the stated light has been absorbed by the biological tissue. A light reception output from the photodiode is amplified by an amplifier, and then distributed and inputted to a computing unit in synchronization with the output of the oscillation circuit using a multiplexer. Based on DC components and pulsation components in respective wavelengths obtained from the light reception output of the photodiode, the computing unit calculates a ratio $\Phi$ of the pulsation components of the respective absorbances resulting from an artery blood flow, and then calculates an arterial blood oxygen saturation from the ratio $\Phi$.

Patent Document 1: Japanese Patent No. 3116252

Incidentally, external light from sources aside from the light-emitting diodes (a light-emitting element) (sunlight, fluorescent lamp light, or the like, for example) sometimes enter into the photodiode (a light-receiving element). There is a risk that such external light will combine with the light originally to be detected, namely the light that has passed through the biological body or that has been reflected by the biological body, and lead to a drop in the signal-to-noise ratio (S/N ratio) of the detection signal.

According to the pulse oximeter of Patent Document 1, when external light has entered the light-receiving element in such a combined manner and the external light component (a noise component) has significantly increased, the amplifier output saturates and the pulsation component (a signal component) can no longer be accurately extracted. Meanwhile, if an amplification rate of the amplifier is reduced to prevent the output saturation, the amplitude of the pulsation component will also drop, resulting in a risk that the accuracy of detecting the oxygen saturation will drop. In the case where the signal is encoded including the external noise component, it will be necessary for the resolution of an A/D converter or the like to be sufficiently high with respect to the pulsation component, which leads to an increase in costs. What is needed, therefore, is a technique that enables an improvement in the signal-to-noise ratio of a detection signal obtained by a light-receiving element and amplified by an amplifier.

SUMMARY OF THE INVENTION

Having been conceived to solve the aforementioned problems, it is an object of the present invention to provide a biological sensor capable of improving the signal-to-noise ratio of a detection signal obtained by a light-receiving element and amplified by an amplifier.

A biological sensor according to the present invention includes a driving signal generating means that generates a driving signal, a light-emitting element that emits light in response to the driving signal generated by the driving signal generating means, a light-receiving element that outputs a detection signal based on an intensity of received light, an amplifying means including an amplifier that amplifies the detection signal outputted from the light-receiving element, an offset means that generates an offset voltage for offsetting a reference potential of the amplifier when amplifying the detection signal and applies the offset voltage to the amplifier, and a computing means that obtains biological information by processing the detection signal amplified by the amplifying means.

According to the biological sensor of the present invention, the reference potential of the amplifier when the detection signal is amplified is offset. Here, a noise component such as external light combines, or overlaps with the detection signal as a DC component, and thus offsetting the reference potential of the amplifier makes it possible to cut the noise component. As such, the signal-to-noise ratio of the detection signal obtained by the light-receiving element and amplified by the amplifier (the amplifying means) can be improved.

In the biological sensor according to the present invention, it is preferable that the driving signal generating means generate a pulse-form driving signal, and the offset means generate and apply a pulse-form offset voltage synchronized with the pulse-form driving signal generated by the driving signal generating means.

In this case, the light-emitting element is driven in a blinking manner by the pulse-form driving signal, and thus the amount of power consumed thereby can be reduced as compared to a case where the light-emitting element is constantly on. Furthermore, the pulse-form offset voltage synchronized with the pulse-form driving signal is applied to the operational amplifier, and thus the noise component can be cut from the detection signal obtained by the light-receiving element when the light-emitting element is on.

In the biological sensor according to the present invention, it is preferable that the offset means include an offset signal generating means that generates an offset signal, and a voltage dividing means that includes a plurality of resistors and that generates the offset voltage by voltage-dividing the offset signal generated by the offset signal generating means.

In this case, using the offset signal generating means and the voltage dividing means in combination with each other makes it possible to improve the accuracy of the offset voltage applied to the amplifier. Accordingly, the noise component can be cut with accuracy.

It is preferable that the biological sensor according to the present invention further include a varying means that varies an amplification rate of the amplifying means based on an amplitude of an AC component of the detection signal amplified by the amplifying means.

By employing this configuration, the amplification rate of the amplifying means can be varied (adjusted) based on the amplitude of the AC component of the detection signal, or in other words, based on the amplitude of the signal component. Accordingly, the amplification rate of the amplifying means (amplifier) can be increased by the amount at which the noise component is cut (that is, the amount by which the signal-to-noise ratio is improved). As a result, the amplitude of the signal component can be increased.

It is preferable that the biological sensor according to the present invention further include a light-emitting element that outputs light of a different wavelength from the aforementioned light-emitting element; the driving signal generating means generate pulse-form driving signals having mutually different timings for each of the plurality of light-emitting elements; the offset means generate pulse-form offset voltages independent of each other in synchronization with the respective pulse-form driving signals outputted at mutually different timings, and apply the offset voltages.

According to this configuration, the pulsed light outputted from the plurality of light-emitting elements can be received by the single light-receiving element. The noise component can be cut from each instance of the light outputted from the plurality of light-emitting elements at mutually different wavelengths. Accordingly, the signal-to-noise ratio can be improved for each instance of the pulsed light outputted from the plurality of light-emitting elements.

In the biological sensor according to the present invention, it is preferable that the amplifying means include a plurality of amplifiers connected in multiple stages, and the offset means apply the offset voltage to the amplifier in or after the second stage.

In this case, the detection signal amplified in a former stage is inputted to the amplifier in the second or subsequent stage, and thus a greater offset voltage is applied to that amplifier in order to cut the noise component. Accordingly, a lower-resolution D/A converter, a lower-precision resistor, or the like can be used as the offset means, and costs can be reduced as a result.

In the biological sensor according to the present invention, it is preferable that the offset signal generating means vary the offset signal based on a voltage value of a DC component of the detection signal amplified by the amplifying means.

In this case, the offset signal is varied based on the DC component of the detection signal. In other words, the offset voltage for cutting the noise component can be varied (adjusted) based on the magnitude of that noise component. Accordingly, the noise component can be effectively cut and the signal-to-noise ratio can be further improved.

According to the present invention, the signal-to-noise ratio of a detection signal obtained by a light-receiving element and amplified by an amplifier can be improved.

DETAILED DESCRIPTION OF THE EXEMPLARY EMBODIMENTS

Figure 1:
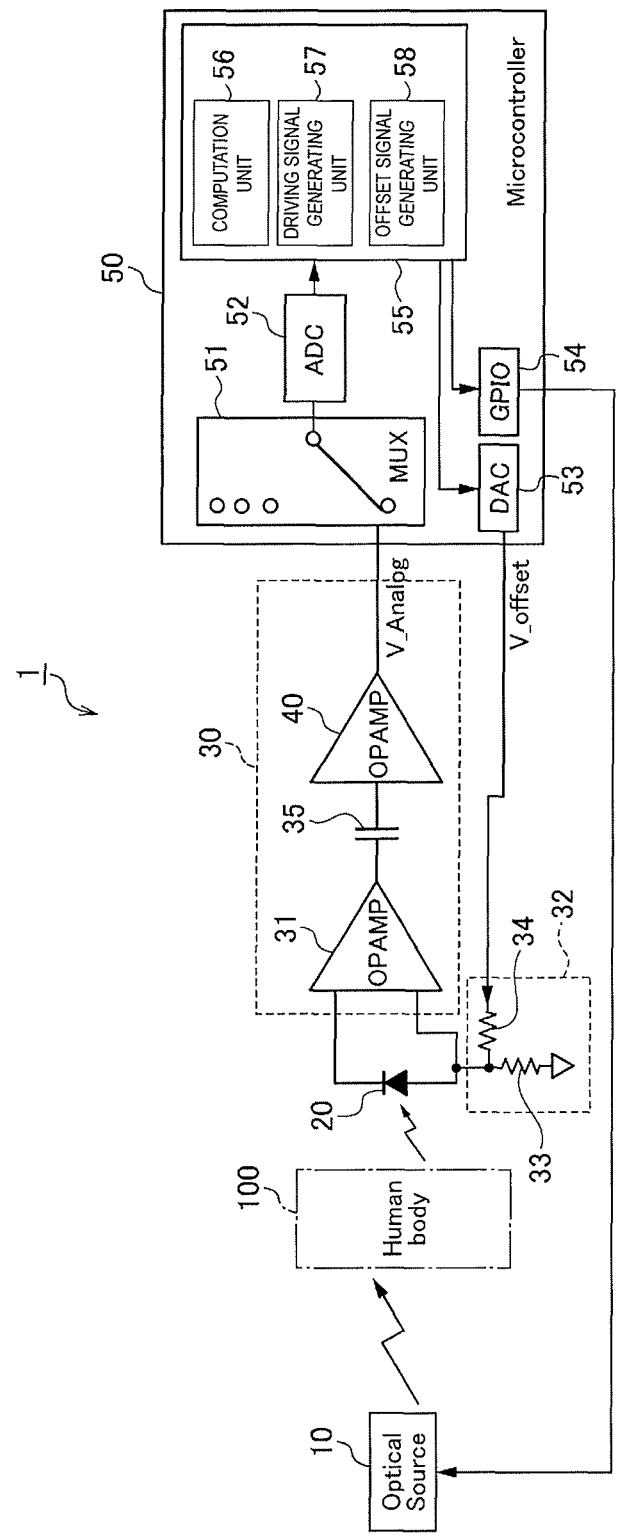
FIG. 1 is a block diagram illustrating the configuration of a biological sensor according to a first embodiment.

Hereinafter, preferred embodiments of the present invention will be described in detail with reference to the drawings. In the drawings, the same reference numerals are used for identical or corresponding portions. Furthermore, the same reference numerals are appended to identical elements and redundant descriptions thereof will be omitted.

First Embodiment

Figure 2:
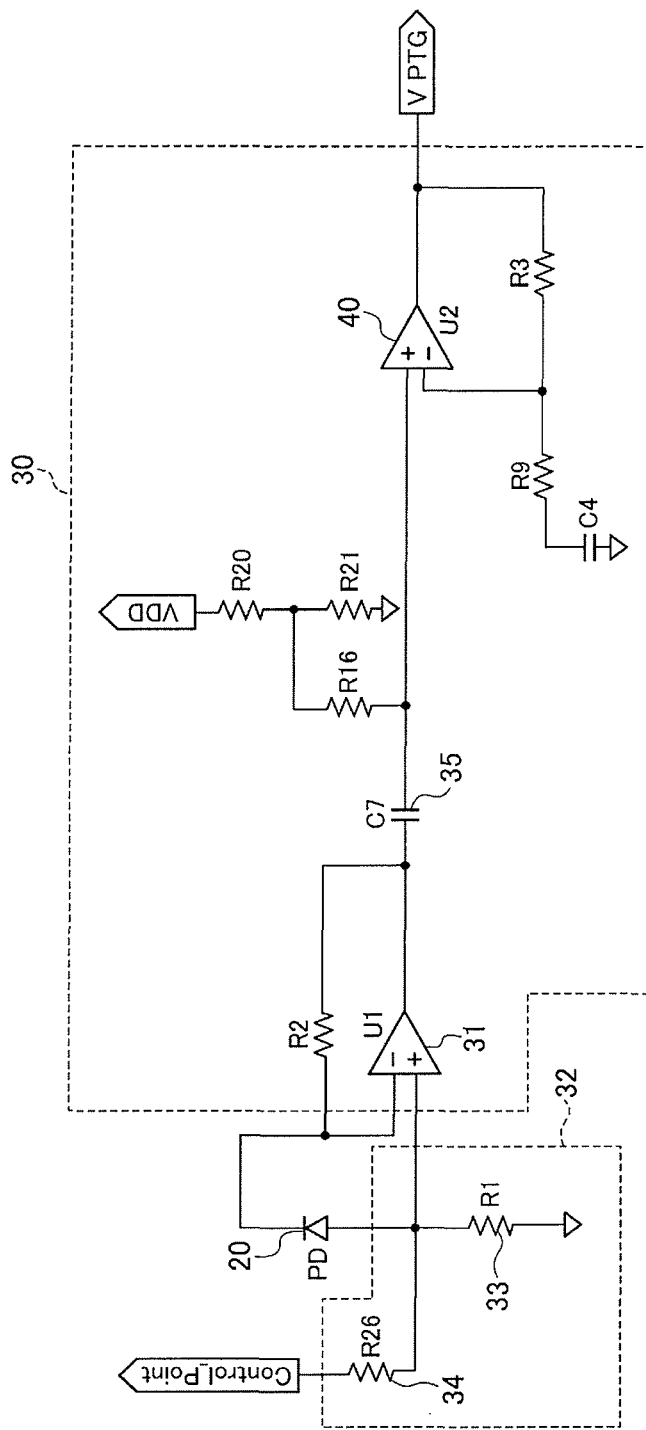
FIG. 2 is a circuit diagram illustrating an input section that partially configures the biological sensor according to the first embodiment.

First, the configuration of a biological sensor 1 according to a first embodiment will be described with reference to FIGS. 1 and 2. Here, FIG. 1 is a block diagram illustrating the configuration of the biological sensor 1. FIG. 2, meanwhile, is a circuit diagram illustrating an input section that partially configures the biological sensor 1.

The biological sensor 1 is a sensor that uses light absorption characteristics of bloodstream hemoglobin to optically detect a photoelectric pulse wave signal and measure biological information such as a pulse. As such, the biological sensor 1 is primarily configured of a light-emitting element (optical source) 10, a light-receiving element 20, an amplifying unit 30, a microcontroller 50, and so on.

The light-emitting element 10 emits light based on a pulse-form driving signal outputted from an output port 54 of the microcontroller 50. For example, an LED, a VCSEL (Vertical Cavity Surface Emitting LASER), a resonator-type LED, or the like can be used as the light-emitting element 10. Note that a 600 Hz pulse signal is used as the driving signal in the present embodiment.

The light-receiving element 20 outputs a detection signal based on the intensity of incident light that has been emitted from the light-emitting element 10 and then passed through a human body 100 such as a fingertip or reflected by the human body 100. For example, a photodiode, a phototransistor, or the like can be preferably used as the light-receiving element 20. A photodiode is used as the light-receiving element 20 in the present embodiment. The light-receiving element (photodiode) 20 is connected to the amplifying unit 30, and the detection signal (photoelectric pulse wave signal) obtained by the light-receiving element (photodiode) 20 is outputted to the amplifying unit 30.

The amplifying unit 30 includes two operational amplifiers (op-amps) 31 and 40 connected in multiple stages (two stages, in the present embodiment), and amplifies the detection signal (photoelectric pulse wave signal) outputted from the light-receiving element (photodiode) 20.

More specifically, a cathode electrode of the photodiode 20 is connected to an inverting input (−) terminal of the operational amplifier 31 in the former stage (a first stage) (called a "first operational amplifier" hereinafter). Meanwhile, an anode terminal of the photodiode 20 is connected to a non-inverting input (+) terminal of the first operational amplifier 31. A voltage dividing resistor group 32 (corresponding to a voltage dividing means claimed in the claims) that divides an analog signal outputted from a D/A converter 53 of the microcontroller 50 and applies the resulting signal to the non-inverting input (+) terminal of the operational amplifier 31 is connected to the anode terminal of the photodiode 20.

More specifically, the voltage dividing resistor group 32 includes a first resistor 33 whose one end is connected to the anode terminal of the photodiode 20 and the non-inverting input (+) terminal of the first operational amplifier 31 and whose other end is connected to a ground, and a second resistor 34 whose one end is connected to the one end of the first resistor 33 and whose other end is connected to an output terminal of the D/A converter 53. Accordingly, a voltage obtained by dividing the analog signal outputted from the D/A converter 53 based on a ratio between a resistance value of the first resistor 33 and a resistance value of the second resistor 34 (that is, an offset voltage) arises at a point of connection between the first resistor 33 and the second resistor 34 (that is, the anode terminal of the photodiode 20 and the non-inverting input (+) terminal of the first operational amplifier 31). A reference potential (operating point) of the first operational amplifier 31 when the detection signal is amplified is thus offset by this offset voltage.

A method for setting the offset voltage (correction voltage) will be described next. Looking at the output end of the amplifying unit 30, for example, in the case where a DC component (noise component) is to be corrected (cut) by 1 V, and assuming an amplification rate of the amplifying unit 30 (that is, the product of the amplification rate of the operational amplifier 31 and the amplification rate of the operational amplifier 40) is 100 times, an offset voltage of $\frac{1}{100}$ (V), namely 0.01 (V), may be applied. In other words, in this case, the resistance values of the first resistor 33 and the second resistor 34, as well as the output voltage of the D/A converter 53, are set and adjusted so that the offset voltage reaches 0.01 (V).

An output terminal of the first operational amplifier 31 is connected to an input terminal (a non-inverting input (+) terminal) of the second operational amplifier 40 via a capacitor 35 (in other words, is AC-coupled). The detection signal amplified by the first operational amplifier 31 has its DC component removed by the capacitor 35, and is then once again amplified by the operational amplifier 40 in the latter stage (a second stage) (called a "second operational amplifier" hereinafter). An output end of the second operational amplifier 40 is connected to the microcontroller 50, and the amplified detection signal (photoelectric pulse wave signal) is outputted to the microcontroller 50.

The microcontroller 50 obtains biological information such as the pulse of a user by processing the detection signal (photoelectric pulse wave signal) detected by the photodiode 20 and amplified by the amplifying unit 30. The microcontroller 50 also outputs a driving signal to the light-emitting element 10 and outputs the offset signal to the voltage dividing resistor group 32. Accordingly, the microcontroller 50 is configured so as to include a multiplexer 51 and an A/D converter 52 serving as an input interface, a CPU 55 that carries out computational processes on a detection signal inputted via the A/D converter 52, a ROM that stores programs and data for causing the CPU to execute various processes, a RAM that temporarily stores various types of data such as computational results, the D/A converter 53 that outputs the offset signal (analog signal), the output port 54 that outputs the driving signal, and so on.

The microcontroller 50 also realizes the functions of a computation unit 56, a driving signal generating unit 57, and an offset signal generating unit 58 by the CPU 55 executing the programs stored in the ROM. Note that the A/D converter 52, the D/A converter 53, the CPU 55, the ROM, the RAM, and so on may be configured of independent chips.

The multiplexer 51 selects and switches among input ports for A/D conversion. The multiplexer 51 switches among input ports based on a control signal from the CPU. The detection signal (photoelectric pulse wave signal) from the input port selected by the multiplexer 51 is sent to the A/D converter 52.

The A/D converter 52 converts the detection signal (photoelectric pulse wave signal) from the input port selected by the multiplexer 51 into digital data at a predetermined sampling period. The digitized detection signal is outputted to the computation unit 56.

The computation unit 56 obtains the biological information such as a pulse by processing the obtained detection signal (photoelectric pulse wave signal). In other words, the computation unit 56 functions as a computing means claimed in the claims. Note that the obtained biological information such as a pulse is outputted to the exterior or stored in the aforementioned RAM or the like.

The driving signal generating unit 57 generates a pulse-form driving signal that drives the light-emitting element 10, and outputs the generated driving signal via the output port 54. In other words, the driving signal generating unit 57 functions as a driving signal generating means claimed in the claims. The driving signal generating unit 57 is set to generate a pulse wave having a frequency of 600 Hz as the driving signal in the present embodiment.

The offset signal generating unit 58 generates a pulse-form offset signal (digital data) synchronized with the pulse-form driving signal outputted by the driving signal generating unit 57, based on a voltage-dividing ratio determined by the resistance values of the first resistor 33 and the second resistor 34. For example, in the case where an offset voltage of 0.01 (V) is to be applied to the first operational amplifier 31, and the voltage-dividing ratio of the voltage dividing resistor group 32 is set to $\frac{1}{5}$, for example, the offset signal (digital data) is generated so that 0.05 (V) is outputted from the D/A converter 53.

The offset signal (digital data) generated by the offset signal generating unit 58 is converted into an analog signal by the D/A converter 53 and is then outputted to the voltage dividing resistor group 32. In other words, the offset signal generating unit 58, the D/A converter 53, and the voltage dividing resistor group 32 function as an offset means claimed in the claims.

By employing the aforementioned configuration, in the biological sensor 1 according to the present embodiment, a pulse signal having a frequency of 600 Hz, for example, is generated by the driving signal generating unit 57 of the microcontroller 50 and outputted from the output port 54. The light-emitting element 10 to which the pulse signal is applied emits pulsed light at a predetermined wavelength in response to the pulse signal. The pulsed light that is emitted from the light-emitting element 10 and that passes through the human body 100 such as a fingertip or is reflected by the human body 100, enters the light-receiving element 20 and is converted into an electrical signal (detection signal) by the light-receiving element 20.

Meanwhile, the offset signal generating unit 58 of the microcontroller 50 generates the pulse-form offset signal (digital data) that is synchronized with the pulse signal (driving signal). The offset signal is converted into an analog voltage by the D/A converter 53 and is applied to the voltage dividing resistor group 32. Accordingly, a voltage divided based on the ratio between the resistance value of the first resistor 33 and the resistance value of the second resistor 34 that configure the voltage dividing resistor group 32 (that is, the offset voltage) is applied to the point of connection between the anode terminal of the light-receiving element (photodiode) 20 and the non-inverting input terminal of the first operational amplifier 31 that partially configures the amplifying unit 30.

The detection signal obtained by the light-receiving element 20 is amplified by the amplifying unit 30. At this time, a reference potential (operating point) of the first operational amplifier 31 is offset by the offset voltage. Accordingly, a noise component such as external light, appearing as a DC component, that is combined with the detection signal, is cut. The signal-to-noise ratio of the detection signal is improved as a result.

The detection signal amplified by the first operational amplifier 31 is inputted into the microcontroller 50 after being further amplified by the second operational amplifier 40 in the next stage. The detection signal inputted into the microcontroller 50 is supplied to the computation unit 56 via the multiplexer 51 and the A/D converter 52. The detection signal is then processed by the computation unit 56, and the biological information such as a pulse is obtained.

According to the present embodiment as described thus far, the reference potential (operating point) of the first operational amplifier 31 when the detection signal is amplified is offset. Accordingly, a noise component such as external light, appearing as a DC component, that is combined with the detection signal, can be cut. As such, the signal-to-noise ratio of the detection signal obtained by the light-receiving element 20 and amplified by the amplifying unit 30 (the first operational amplifier 31) can be improved. As a result, a range in which no pulse is detected, based on individual differences from measurement subject to measurement subject, can be reduced. In other words, the detection rate can be improved. In addition, low-noise requirements for the amplifying unit 30 can be relaxed, which makes it possible to reduce the cost of the circuit components of which the amplifying unit 30 is configured. The resolution of the A/D converter 52 can furthermore be reduced, which makes it possible to achieve even lower costs.

In addition, according to the present embodiment, the light-emitting element 10 is driven in a blinking manner by the pulse-form driving signal, and thus the amount of power consumed thereby can be reduced as compared to a case where the light-emitting element 10 is constantly on. Furthermore, the pulse-form offset voltage synchronized with the pulse-form driving signal is supplied to the first operational amplifier 31, and thus the noise component can be cut from the detection signal obtained by the light-receiving element 20 when the light-emitting element 10 is on.

Furthermore, according to the present embodiment, the offset voltage can be accurately generated and applied by using the combination of the D/A converter 53 and the voltage dividing resistor group 32, in cases such as where the resolution would be insufficient if only the D/A converter 53 was used, for example. Accordingly, the noise component can be cut with accuracy.

The signal-to-noise ratio improvement effects obtained by applying the offset voltage to the first operational amplifier 31 were confirmed by simulating and taking actual measurements of the analog output voltage outputted from the amplifying unit 30, for both a case where the offset voltage is applied to the first operational amplifier 31 (the present embodiment) and a case where the offset voltage is not applied (a conventional circuit; a comparative example). The signal-to-noise ratio improvement effect obtained by applying the offset voltage to the first operational amplifier 31 will be described next with reference to FIGS. 3 to 6.

Figure 3:
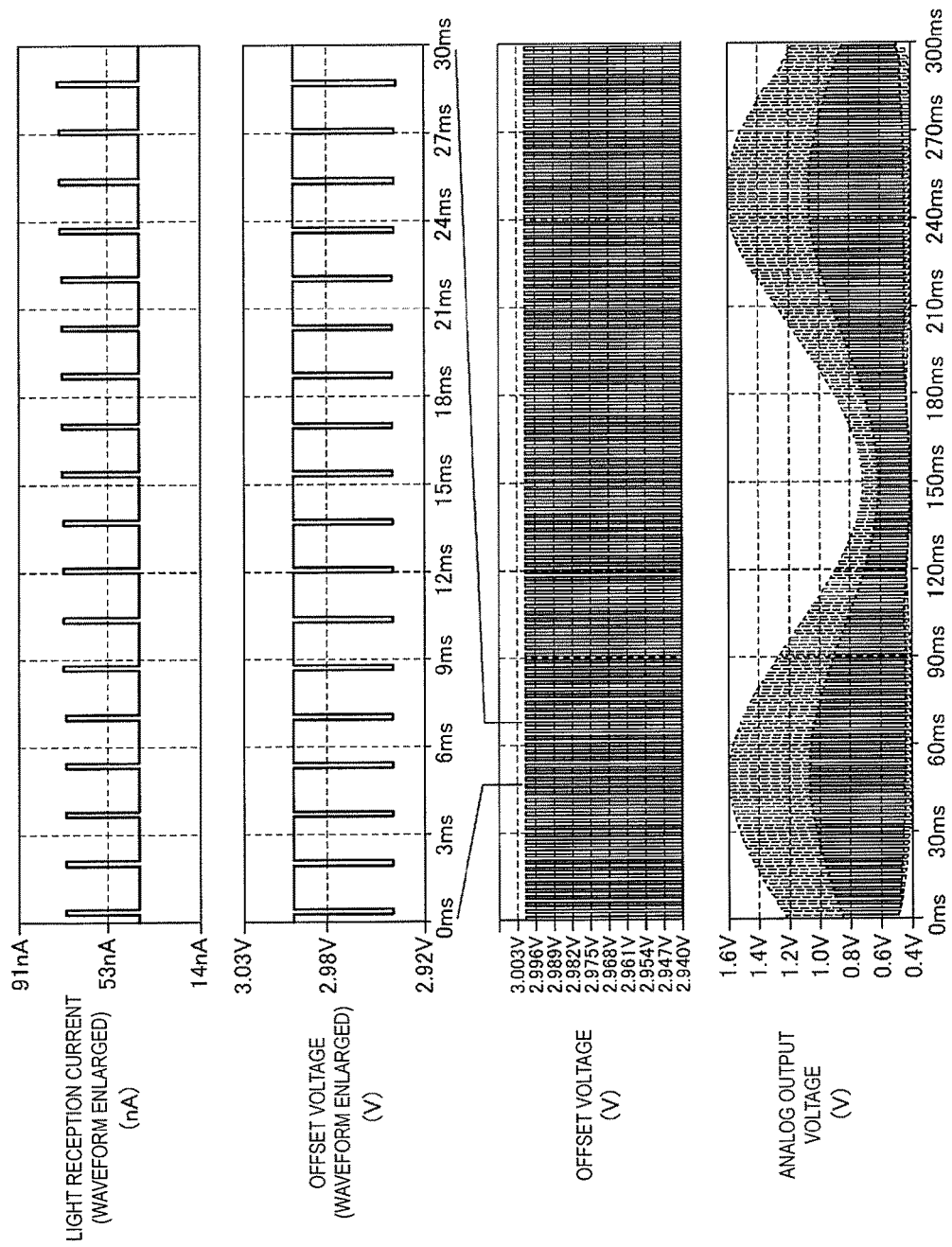
FIG. 3 is a diagram illustrating results of a simulation of an output voltage and the like outputted from an amplifying unit of the biological sensor according to the first embodiment.
Figure 4:
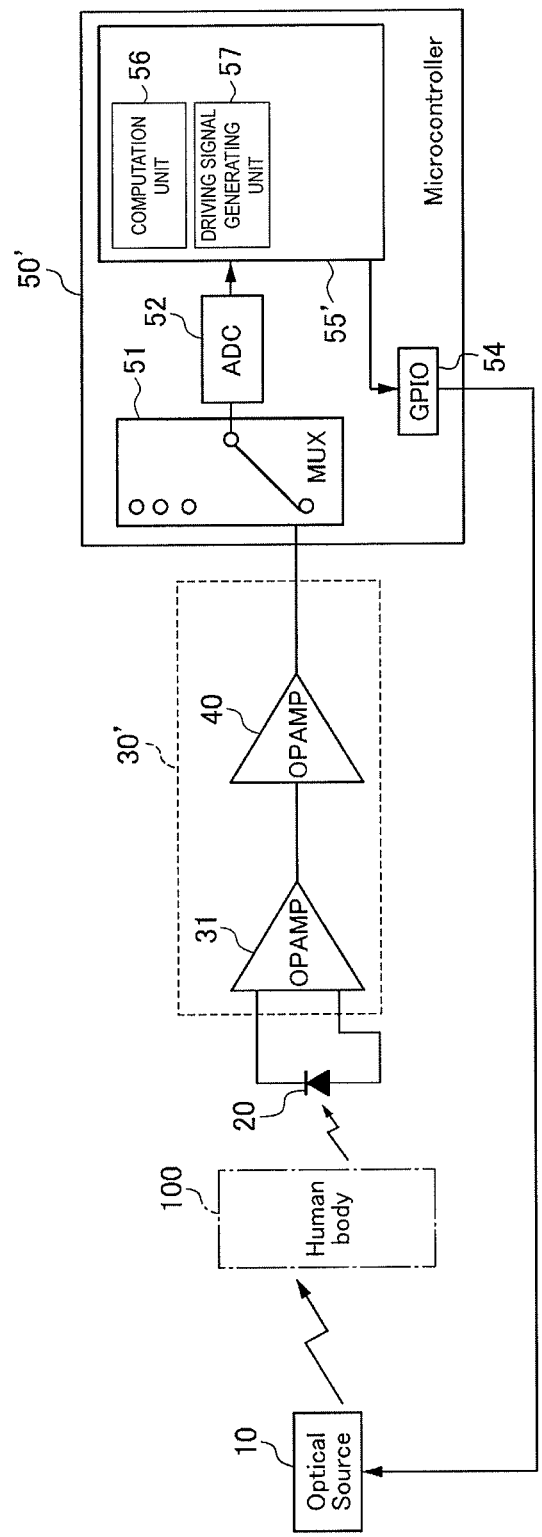
FIG. 4 is a block diagram illustrating the configuration of a biological sensor according to a conventional technique (comparative example).
Figure 5:
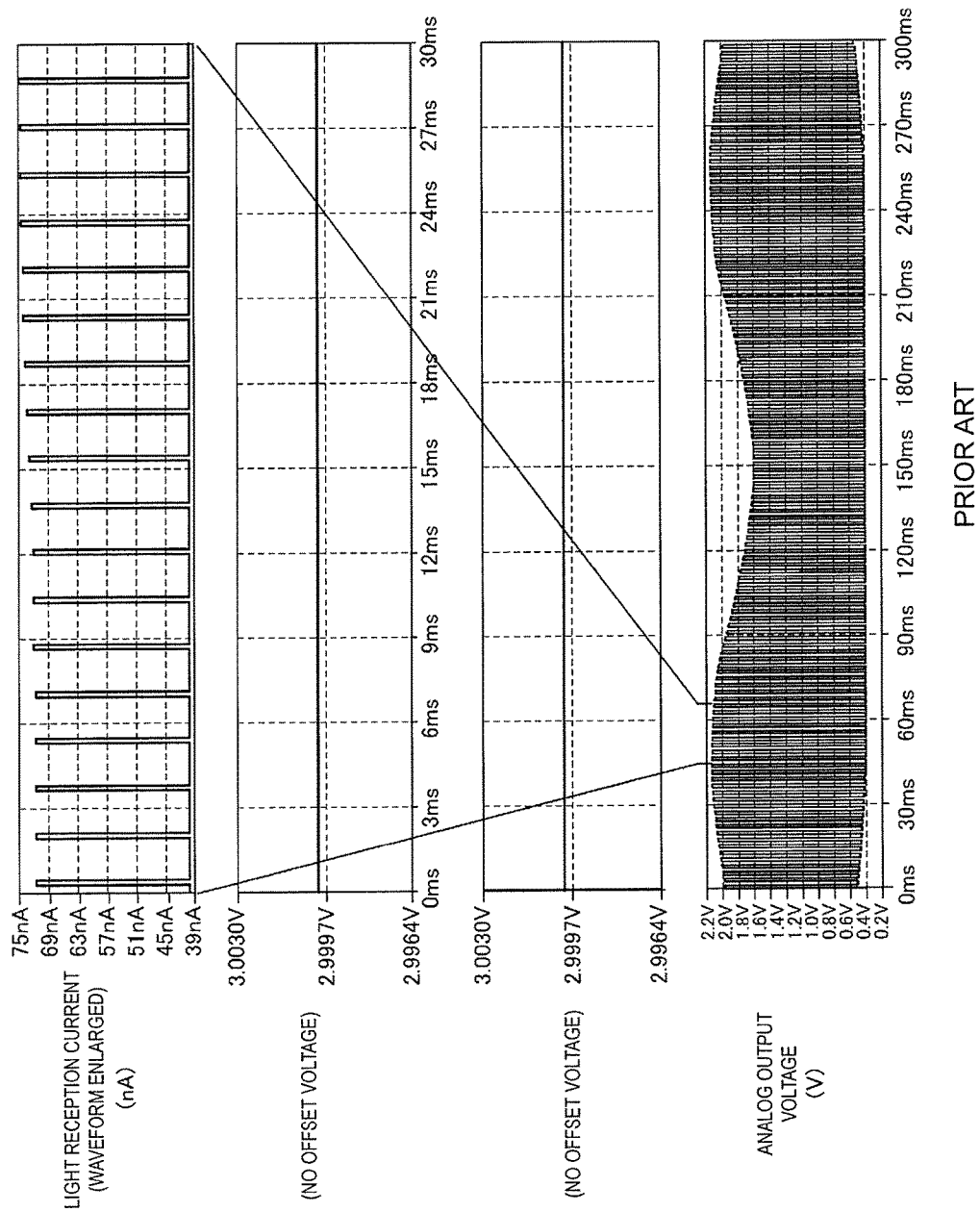
FIG. 5 is a diagram illustrating results of a simulation of an output voltage outputted from an amplifying unit of the biological sensor according to the conventional technique (comparative example).
Figure 6:
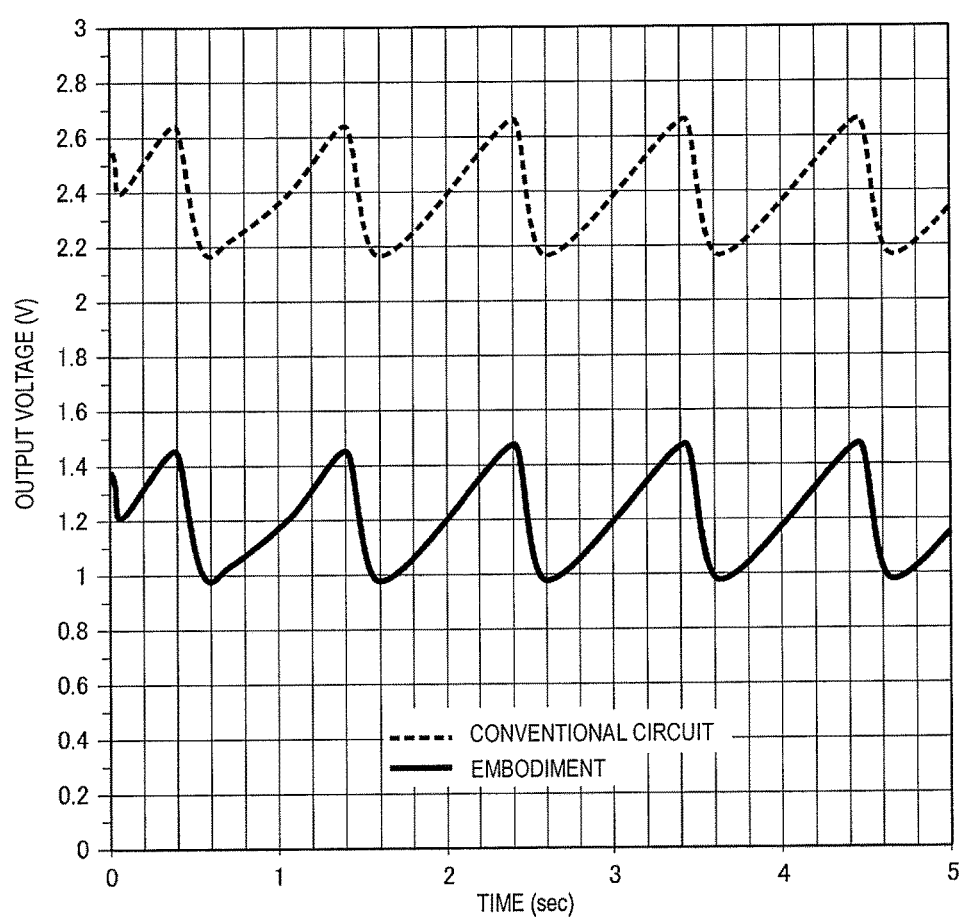
FIG. 6 is a diagram illustrating examples of actual measurements of output voltages outputted from the amplifying unit of the biological sensor according to the first embodiment and from the amplifying unit of the biological sensor according to the conventional technique (comparative example).

FIG. 3 is a diagram illustrating results of a simulation of the detection signal outputted from the amplifying unit 30 of the biological sensor 1 according to the present embodiment. FIG. 4 is a block diagram illustrating the configuration of a biological sensor according to a conventional technique, used as a comparative example. FIG. 5, meanwhile, is a diagram illustrating results of a simulation of an output voltage outputted from an amplifying unit 30' of the biological sensor according to the conventional technique (comparative example) shown in FIG. 4. FIG. 6 is a diagram illustrating examples of actual measurements of output voltages outputted from the amplifying unit 30 of the biological sensor 1 according to the present embodiment and from the amplifying unit 30' of the biological sensor according to the conventional technique (comparative example).

First, the result of simulating the output voltage outputted from the amplifying unit 30 of the biological sensor 1 according to the present embodiment will be described with reference to FIG. 3. FIG. 3 illustrates, in order from the upper section, a waveform (nA) in which a light reception current from the light-receiving element 10 has been enlarged along a time axis, a waveform (V) in which the offset voltage has been enlarged along the time axis, the offset voltage (V), and the analog output voltage (V) from the amplifying unit 30. The horizontal axes in FIG. 3 represent time (ms).

When the light reception current shown in the first section is I-V converted and amplified, and in the case where a pulse-form offset voltage at approximately 0.06 V (−0.06 V due to inversion, with 3 V as a reference) is applied to the first operational amplifier 31 as indicated in the second and third sections, the amplitude (p-p) of the analog output voltage is approximately 0.8 V, as indicated by the solid line in the fourth section. At this time, the amplitude of the detection signal (pulse wave signal) is approximately 0.5 V. Accordingly, the signal-to-noise ratio is 0.5/0.8, or in other words, approximately 62.5%, thus confirming that the signal-to-noise ratio can be improved as compared to the conventional circuit, which will be described later.

A waveform obtained in the case where the amplification rate of the amplifying unit 30 is doubled is indicated by a broken line in the fourth section of FIG. 3. In this case, as indicated by the broken line in the fourth section, it was confirmed that the amplitude of the pulse wave signal was also able to be doubled without degrading the pulse wave signal (detection signal) and without saturating the pulse wave signal.

Next, the results of simulating the output voltage (pulse wave signal) outputted from the amplifying unit 30' of the biological sensor according to the conventional circuit (comparative example) will be described with reference to FIGS. 4 and 5. As described above, FIG. 4 is a block diagram illustrating the configuration of the biological sensor employing the conventional circuit, used as a comparative example. As shown in FIG. 4, this biological sensor does not include the offset signal generating unit 58, the D/A converter 53, or the voltage dividing resistor group 32. Accordingly, the offset voltage that offsets the operating point is not applied to the first operational amplifier 31 provided in the amplifying unit 30'.

FIG. 5 illustrates a result of simulating the output voltage outputted from the amplifying unit 30' of the biological sensor according to the conventional technique (comparative example) shown in FIG. 4. FIG. 5 illustrates, in order from the upper section, a waveform (nA) in which a light reception current from the light-receiving element 10 has been enlarged along a time axis, a waveform (V) in which the offset voltage has been enlarged along the time axis, the offset voltage (V), and the analog output voltage (V) from the amplifying unit 30'. The horizontal axes in FIG. 5 represent time (ms).

When the light reception current shown in the first section is I-V converted and amplified, and in the case where the offset voltage is 0 (3 V, due to the inversion), or in other words, the offset voltage is not applied as indicated in the second and third sections, the amplitude (p-p) of the analog output voltage is approximately 1.8 V, as indicated in the fourth section. At this time, the amplitude of the detection signal (pulse wave) is approximately 0.5 V. The signal-to-noise ratio is thus 0.5/1.8, or in other words, approximately 28%.

Based on the aforementioned results, it was confirmed that the biological sensor 1 according to the present embodiment can improve the signal-to-noise ratio from approximately 28% to approximately 62.5%.

Next, an example of actual measurements of the results confirmed for the signal-to-noise ratio improvement effect provided by the biological sensor 1 according to the present embodiment will be described with reference to FIG. 6. FIG. 6 illustrates examples of actual measurements of the output voltages (analog outputs) outputted from the amplifying unit 30 of the biological sensor 1 according to the present embodiment and from the amplifying unit 30' of the biological sensor according to the conventional technique (comparative example) illustrated in FIG. 4. The horizontal axis in FIG. 6 represents time (sec), and the vertical axis represents the analog output voltage (V) of the amplifying unit 30 (or the amplifying unit 30'). Meanwhile, in FIG. 6, a measurement result according to the present embodiment is indicated by a solid line, whereas a measurement result for the conventional circuit (see FIG. 4) is indicated by a broken line.

As shown in FIG. 6, compared to the case where the conventional circuit is used, it was confirmed that the analog output from the amplifying unit 30 according to the present embodiment is offset (reduced) by approximately 1.1 V overall without the amplitude thereof varying. In other words, it was successfully confirmed that the light reception voltage range was able to be reduced by approximately half (in other words, the signal-to-noise ratio was able to be improved) without degrading the pulse amplitude.

Second Embodiment

Next, the configuration of a biological sensor 2 according to a second embodiment will be described with reference to FIG. 7. Here, descriptions of configurations that are identical or similar to those in the biological sensor 1 according to the aforementioned first embodiment will be simplified or omitted, and primarily the points of difference will be described.

Figure 7:
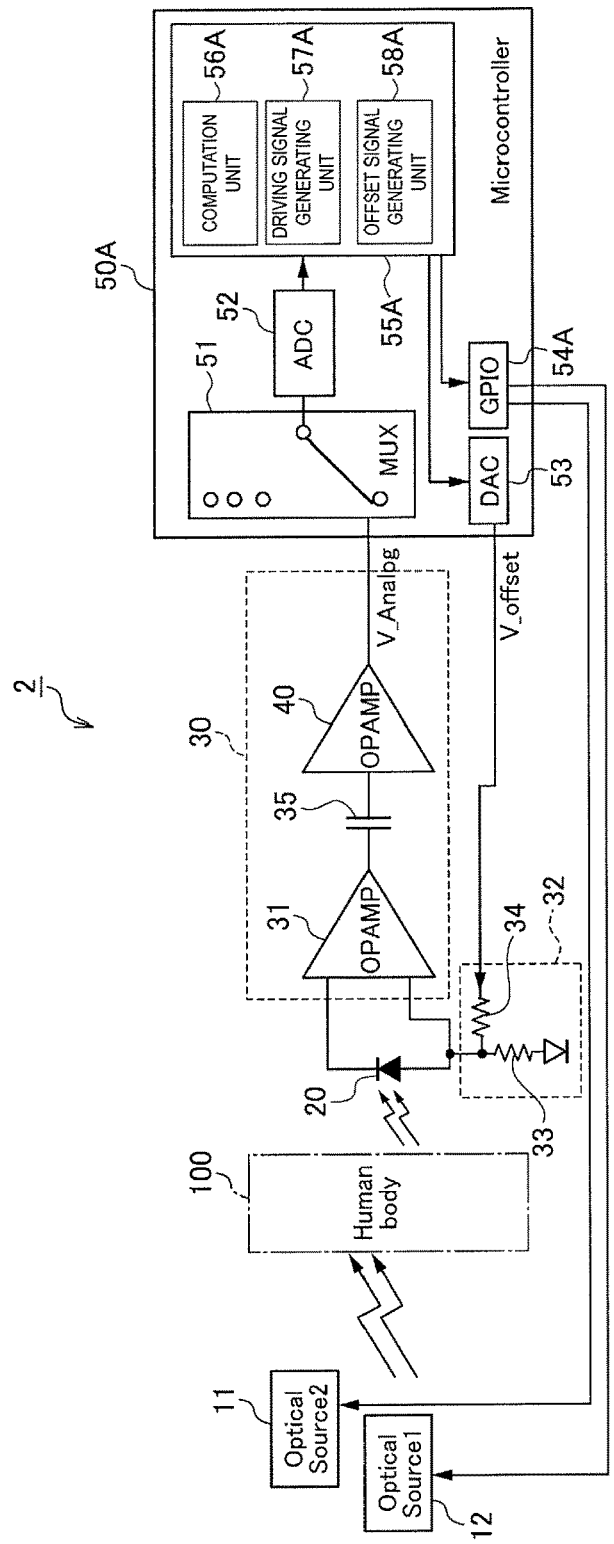
FIG. 7 is a block diagram illustrating the configuration of a biological sensor according to a second embodiment.

FIG. 7 is a block diagram illustrating the configuration of the biological sensor 2 according to the second embodiment. In FIG. 7, constituent elements that are identical or equivalent to those in the first embodiment have been given the same reference numerals.

The biological sensor 2 differs from the aforementioned biological sensor 1 in that two light-emitting elements (optical sources) 11 and 12 are provided. The two light-emitting elements 11 and 12 emit respectively different wavelengths of light in order to obtain an abundance ratio between oxygenated hemoglobin and reduced hemoglobin, which indicates the blood oxygen saturation. For example, the one light-emitting element 11 emits near-infrared light whose absorption coefficient with respect to oxygenated hemoglobin is high (940 nm, for example). The other light-emitting element 12 emits near-red light whose absorption coefficient with respect to reduced hemoglobin is high (660 nm, for example).

A driving signal generating unit 57A that partially configures a microcontroller 50A generates pulse-form driving signals (pulse signals) having the same frequency (600 Hz, for example) but mutually different timings for the two light-emitting elements 11 and 12. The generated pulse signals having mutually different timings are outputted to the light-emitting element 11 and the light-emitting element 12 via an output port 54A.

Meanwhile, an offset signal generating unit 58A generates pulse-form offset signals (digital data), whose voltage values are adjusted independently of each other, in synchronization with the aforementioned driving signals (pulse signals). The generated offset signals (digital data) are converted into analog signals by the D/A converter 53, voltage-divided by the voltage dividing resistor group 32, and applied to the non-inverting input terminal of the first operational amplifier 31.

A computation unit 56A computes an abundance ratio (absorbance ratio) between the oxygenated hemoglobin and the reduced hemoglobin from the detection signals of the respective wavelengths, and finds an oxygen saturation. The other configurations are the same as or similar to those in the biological sensor 1, and thus detailed descriptions thereof will be omitted.

In the biological sensor 2 according to the present embodiment, the driving signal generating unit 57A generates and outputs the pulse-form driving signals (pulse signals) having mutually different timings. Pulsed light having different wavelengths is then outputted from the two light-emitting elements 11 and 12 at respectively different timings. The pulsed light that is emitted from the light-emitting elements 11 and 12 and that passes through the human body 100 such as a fingertip or is reflected by the human body 100 is then received by the light-receiving element 20 and converted into an electrical signal (detection signal).

Meanwhile, the offset signal generating unit 58A generates and outputs the pulse-form offset voltages (digital data), whose voltage values are adjusted independently of each other, in synchronization with both the driving signals (pulse signals). The offset voltage is converted into an analog voltage by the D/A converter 53 and is applied to the voltage dividing resistor group 32. Accordingly, a voltage divided based on the ratio between the resistance value of the first resistor 33 and the resistance value of the second resistor 34 that configure the voltage dividing resistor group 32 (that is, the offset voltage) is applied to the point of connection between the anode terminal of the light-receiving element (photodiode) 20 and the non-inverting input terminal of the first operational amplifier 31 that partially configures the amplifying unit 30.

The detection signal obtained by the light-receiving element 20 is amplified by the amplifying unit 30. At this time, a reference potential (operating point) of the first operational amplifier 31 is offset by the offset voltage. Accordingly, a noise component such as external light, appearing as a DC component, that is combined with the detection signal, is cut. The signal-to-noise ratios of the detection signals for each instance of pulsed light outputted from the two light-emitting elements 11 and 12 at different wavelengths are improved as a result.

The detection signals amplified by the first operational amplifier 31 are inputted into the microcontroller 50A after being further amplified by the second operational amplifier 40 in the next stage. The detection signals inputted into the microcontroller 50A are supplied to the computation unit 56A via the multiplexer 51 and the A/D converter 52. The detection signals of each wavelength are then processed by the computation unit 56, and the biological information such as the oxygen saturation is obtained from the absorbance ratio for each wavelength, for example.

According to the present embodiment, the pulsed light outputted from the two light-emitting elements 11 and 12 can be received by the single light-receiving element 20. The noise component can be cut from each instance of the pulsed light outputted from the two light-emitting elements 11 and 12 at mutually different wavelengths. Accordingly, the signal-to-noise ratio can be improved for each instance of the pulsed light outputted from the two light-emitting elements 11 and 12. As a result, for example, the absorbance ratio for each wavelength can be measured more accurately, and the oxygen saturation can be detected with a higher degree of accuracy.

Third Embodiment

Figure 8:
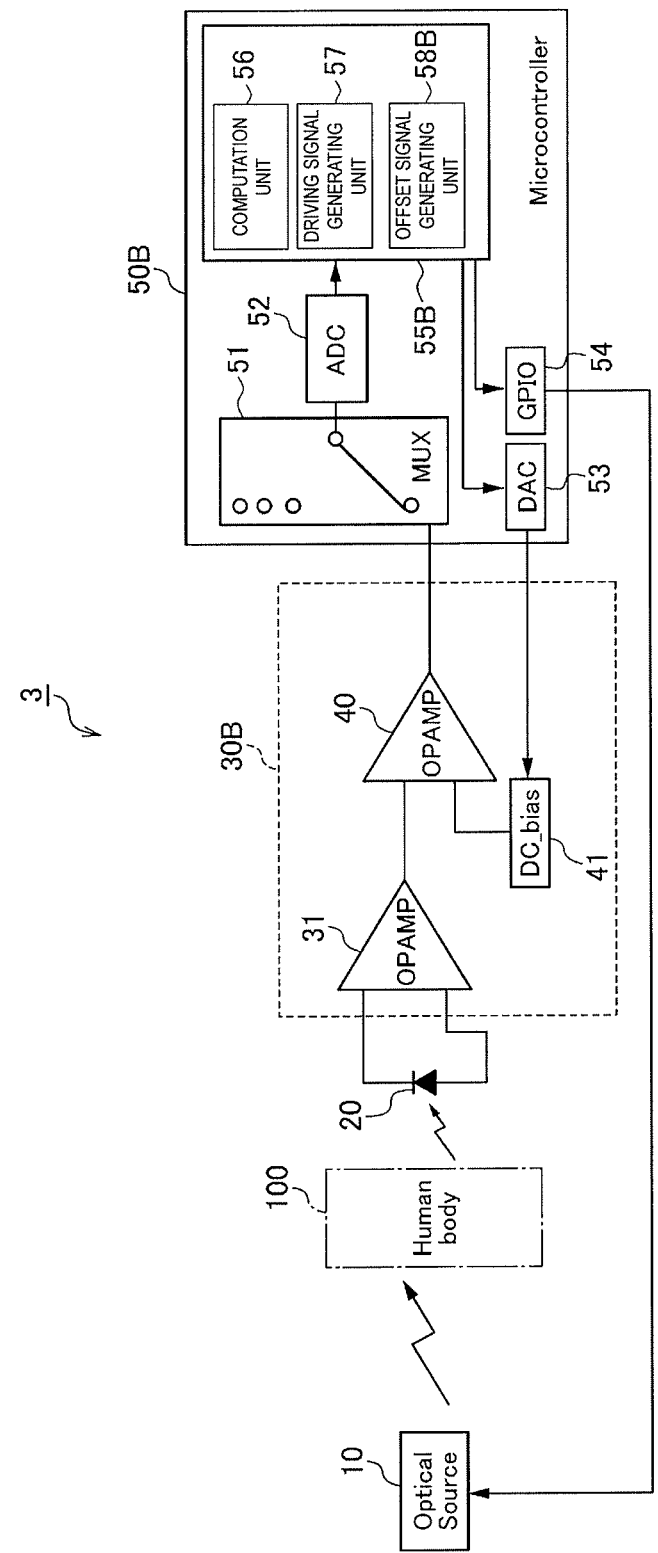
FIG. 8 is a block diagram illustrating the configuration of a biological sensor according to a third embodiment.

Next, the configuration of a biological sensor 3 according to a third embodiment will be described with reference to FIG. 8. Here, descriptions of configurations that are identical or similar to those in the biological sensor 1 according to the aforementioned first embodiment will be simplified or omitted, and primarily the points of difference will be described. FIG. 8 is a block diagram illustrating the configuration of the biological sensor 3 according to the third embodiment. In FIG. 8, constituent elements that are identical or equivalent to those in the first embodiment have been given the same reference numerals.

Although the offset voltage is applied to the non-inverting input of the first operational amplifier 31 in the aforementioned biological sensor 1, the biological sensor 3 differs from the biological sensor 1 in that the offset voltage is applied to an inverting input terminal of the second operational amplifier 40. In this case, the second operational amplifier 40 operates as a differential amplifier circuit that takes the offset voltage as a bias voltage. Note that a circuit identical to the aforementioned voltage dividing resistor group 32, for example, can be used as an offset application circuit 41 shown in FIG. 8. The other configurations are the same as or similar to those in the biological sensor 1, and thus detailed descriptions thereof will be omitted.

In the present embodiment, an offset signal generating unit 58B generates the offset signal based only on the amplification rate of the second operational amplifier 40. Accordingly, in the case where the voltage-dividing ratio of the offset application circuit 41 is the same as in the first embodiment, a voltage obtained by multiplying the offset voltage set in the first embodiment by the amplification rate of the first operational amplifier 31 is applied to the second operational amplifier 40.

According to the present embodiment, the detection signal amplified in the former stage (by the first operational amplifier 31) is inputted into the second operational amplifier 40 in the latter stage, and thus a greater offset voltage (bias voltage) is applied to the second operational amplifier 40 in order to cut the noise component. Accordingly, a lower-resolution D/A converter, a lower-precision resistor, or the like can be used to set and adjust the offset voltage, for example. This makes it possible to further reduce the cost of the sensor.

Note that in the present embodiment, the configuration may be such that the offset signal generating unit 58B varies the offset voltage applied to the second operational amplifier 40 based on a voltage value of the DC component (a noise potential) of the detection signal amplified by an amplifying unit 30B. In this case, the offset voltage for cutting the noise component can be varied and adjusted based on the magnitude (potential) of that noise component, which makes it possible to more effectively cut the noise component and further improve the signal-to-noise ratio.

Fourth Embodiment

Figure 9:
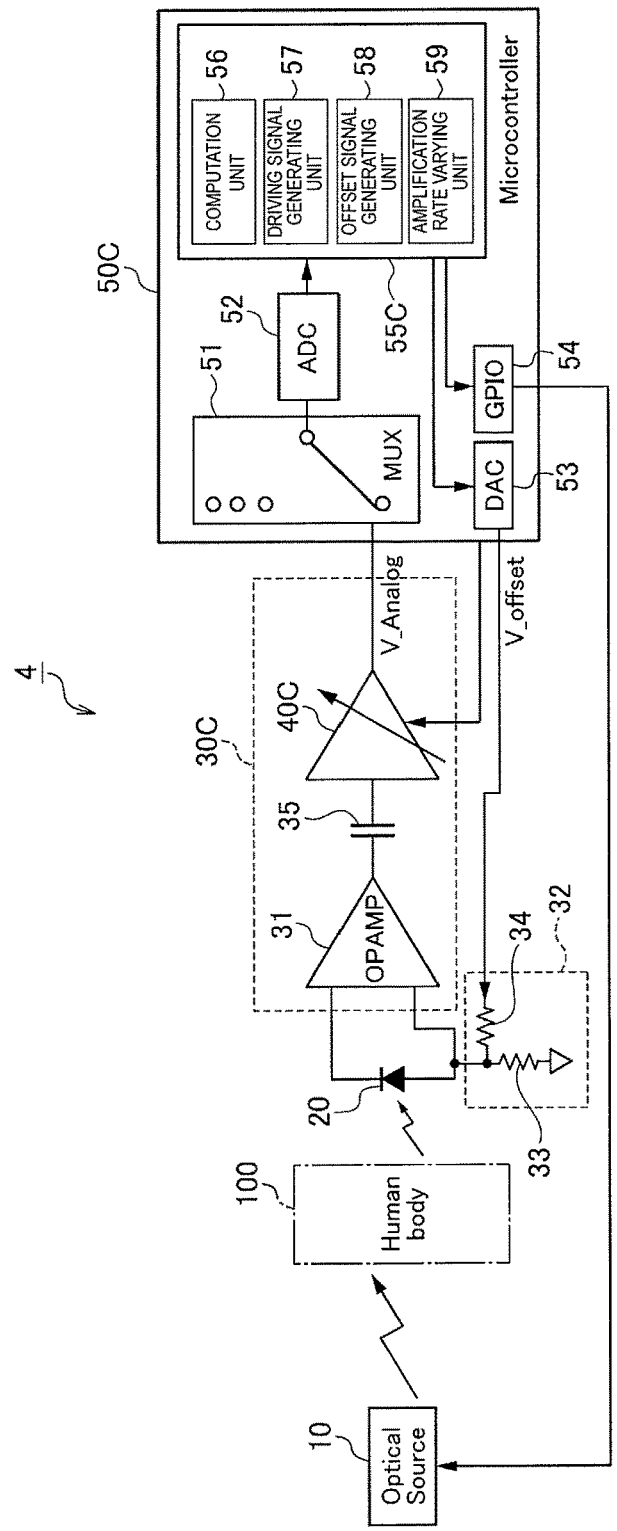
FIG. 9 is a block diagram illustrating the configuration of a biological sensor according to a fourth embodiment.

Next, the configuration of a biological sensor 4 according to a fourth embodiment will be described with reference to FIG. 9. Here, descriptions of configurations that are identical or similar to those in the biological sensor 1 according to the aforementioned first embodiment will be simplified or omitted, and primarily the points of difference will be described. FIG. 9 is a block diagram illustrating the configuration of the biological sensor 4 according to the fourth embodiment. In FIG. 9, constituent elements that are identical or equivalent to those in the first embodiment have been given the same reference numerals.

The biological sensor 4 differs from the aforementioned biological sensor 1 in that an amplification rate varying unit 59 (corresponding to a varying unit claimed in the claims) that varies an amplification rate of, for example, a second operational amplifier 40C that partially configures an amplifying unit 30C based on the amplitude of an AC component of a detection signal amplified by the amplifying unit 30C (in other words, the amplitude of a pulse wave component) is further provided. The other configurations are the same as or similar to those in the biological sensor 1, and thus detailed descriptions thereof will be omitted.

In this case, for example, a variable signal generated by the amplification rate varying unit 59 is converted into an analog signal by a D/A converter (not shown) and outputted to the second operational amplifier 40C. The second operational amplifier 40C varies the amplification rate based on that analog signal.

According to the present embodiment, the amplification rate of the amplifying unit 30C (the second operational amplifier 40C) can be varied and adjusted based on the amplitude of an AC component of the detection signal, or in other words, the amplitude of a signal component (a pulse wave component). Accordingly, the amplification rate of the amplifying unit 30C can be increased by the amount at which the noise component is cut (that is, the amount by which the signal-to-noise ratio is improved). Accordingly, the amplitude of the signal component (the pulse wave component) can be increased. In addition, a range in which no pulse is detected, based on individual differences from measurement subject to measurement subject, can be reduced. In other words, the detection rate can be further improved.

Although embodiments of the present invention have been described thus far, the present invention is not intended to be limited to the aforementioned embodiments, and many variations can be carried out thereon. For example, although the aforementioned embodiments describe configurations in which the amplifying unit 30 (30B, 30C) includes the operational amplifiers 31 and 40 in two stages, the configuration may be such that only one, or three or more, stages of operational amplifiers are provided.

Furthermore, although the aforementioned embodiments describe pulse-form driving signals being generated and inputted to the light-emitting element 10 (11, 12) and pulse-form offset voltages being applied to the first operational amplifier 31 or the second operational amplifier 40, the first operational amplifier 31 and the second operational amplifier 40 in the latter stage may be DC-coupled, with a constant driving signal being generated and inputted to the light-emitting element 10 (11, 12) and a constant offset voltage being applied to the first operational amplifier 31 or the second operational amplifier 40.

REFERENCE SIGNS LIST 1, 2, 3, 4 biological sensor
10, 11, 12 light-emitting element (optical source)
20 light-receiving element
30, 30B, 30C amplifying unit
31 first operational amplifier
40, 40C second operational amplifier
32 voltage dividing resistor group
50, 50A, 50B, 50C microcontroller
53 D/A converter
54, 54A output port
55, 55A, 55B, 55C CPU
56, 56A computation unit
57, 57A driving signal generating unit
58, 58A, 58B, 58C offset signal generating unit
59 amplification rate varying unit

The invention claimed is:

1. A biological sensor comprising:
a driving signal generator that generates a driving signal;
a light-emitting element that emits light in response to the driving signal;
a light-receiving element that outputs a detection signal based on an intensity of received light;
an amplifying circuit that includes at least one amplifier and that receives and amplifies the detection signal outputted from the light-receiving element;
an offset generator circuit that generates an offset voltage that is applied to the at least one amplifier to offset a reference potential of the at least one amplifier and to cut a noise component combined with the detection signal; and
a controller configured to control the offset generator circuit to generate the offset voltage based on a magnitude of the noise component and to process the amplified detection signal to obtain biological information.

2. The biological sensor according to claim 1,
wherein the driving signal generator generates a pulse-form driving signal, and
wherein the offset generator circuit generates a pulse-form offset voltage that is synchronized with the pulse-form driving signal.

3. The biological sensor according to claim 1,
wherein the controller is further configured to generate an offset signal, and
wherein the offset generator circuit includes:
a digital to analog converter that converts the generated signal into an analog offset signal; and
a voltage divider coupled to the digital to analog converter and that includes a plurality of resistors that voltage-divide the analog offset signal to generate the offset voltage that is applied to the at least one amplifier.

4. The biological sensor according to claim 3,
wherein the controller is further configured to determine a voltage value of a DC component of the amplified detection signal, and
wherein the offset signal is varied based on the determined voltage value of the DC component of the amplified detection signal.

5. The biological sensor according to claim 3, wherein the light-receiving element is coupled in parallel between an inverting input and a non-inverting input of the amplifier in the amplifying circuit.

6. The biological sensor according to claim 5, wherein the voltage divider applies the offset voltage to the non-inverting input of the amplifier in the amplifying circuit.

7. The biological sensor according to claim 1, wherein the controller is further configured to:
determine an amplitude of the AC component of the amplified detection signal, and
vary an amplification rate of the amplifying circuit based on the determined amplitude of the AC component.

8. The biological sensor according to claim 1, further comprising:
another light-emitting element that outputs light having a different wavelength than the light emitted from the light-emitting element,
wherein the driving signal generator generates pulse-form driving signals having different timings for the light-emitting elements and the another light-emitting element, respectively, and
wherein the offset generator circuit generates independent pulse-form offset voltages in synchronization with the respective pulse-form driving signals.

9. The biological sensor according to claim 1, wherein the amplifying circuit includes a plurality of amplifiers connected in multiple stages.

10. The biological sensor according to claim 9, wherein the offset voltage is applied to the amplifier in a second or later stage of the multiple stages.

11. A method for obtaining biological information, the method comprising:
generating a driving signal;
emitting light from a light-emitting element in response to the driving signal;
detecting an intensity of received light by a light-receiving element and outputting a detection signal based on the intensity of received light;
amplifying, by at least one amplifier, the detection signal outputted from the light-receiving element;
generating an offset voltage based on a magnitude of a noise component combined with the detection signal;
applying the offset voltage to the at least one amplifier to offset a reference potential of the at least one amplifier and to cut the noise component combined with the detection signal; and
processing the amplified detection signal to obtain biological information.

12. The method for obtaining biological information according to claim 11, further comprising:
- generating a pulse-form driving signal; and
- generating a pulse-form offset voltage that is synchronized with the pulse-form driving signal.

13. The method for obtaining biological information according to claim 11, wherein generating the offset voltage comprises:
- generating an offset signal;
- converting, by a digital to analog converter, the generated offset signal to an analog offset signal; and
- voltage dividing the analog offset signal to generate the offset voltage.

14. The method for obtaining biological information according to claim 11, wherein amplifying the detection signal further comprises:
- determining an amplitude of the AC component of the amplified detection signal; and
- varying an amplification rate based on the determined amplitude of the AC component of the amplified detection signal.

15. The method for obtaining biological information according to claim 11, further comprising:
- emitting light from another light-emitting element having a different wavelength than the light emitted from the light-emitting element;
- generating pulse-form driving signals having different timings for the light-emitting elements and the another light-emitting element, respectively; and
- generating independent pulse-form offset voltages in synchronization with the respective pulse-form driving signals.

16. The method for obtaining biological information according to claim 11, wherein amplifying the detection signal further comprises amplifying the detection signal by a plurality of amplifiers connected in multiple stages.

17. The method for obtaining biological information according to claim 16, further comprising applying the offset voltage to the amplifier in a second or later stage of the multiple stages.

18. The method for obtaining biological information according to claim 13, further comprising:
- determining a voltage value of a DC component of the amplified detection signal; and
- varying the offset signal based on the determined voltage value of the DC component of the amplified detection signal.

19. The method for obtaining biological information according to claim 13, wherein the light-receiving element is coupled in parallel between an inverting input and a non-inverting input of the amplifier in the amplifying circuit.

20. The method for obtaining biological information according to claim 19, further comprising applying the offset voltage to the non-inverting input of the amplifier in the amplifying circuit.

* * * * *